United States Patent
Erskine et al.

(10) Patent No.: US 10,119,943 B2
(45) Date of Patent: *Nov. 6, 2018

(54) COUPLANT AND ARRANGEMENT OF COUPLANT, TRANSDUCER, AND CONSTRUCTION COMPONENT

(71) Applicant: AKTIEBOLAGET SKF, Göteborg (SE)

(72) Inventors: Joseph Erskine, Falkirk (GB); Keith Hamilton, Fife (GB); Gerard McGoogan, Scotland (GB); Tim Smith, Fife (GB); Allan Thomson, Lanark (GB); Mairi Joan Torrie, Edinburgh (GB); Sebastian Ziegler, Schweinfurt (DE); Andreas Clemens Van Der Ham, Utrecht (NL)

(73) Assignee: AKTIEBOLAGET SKF, Gothenburg (SE)

( * ) Notice: Subject to any disclaimer, the term of this patent is extended or adjusted under 35 U.S.C. 154(b) by 139 days.

This patent is subject to a terminal disclaimer.

(21) Appl. No.: 14/651,454

(22) PCT Filed: Dec. 12, 2012

(86) PCT No.: PCT/EP2012/075274
§ 371 (c)(1),
(2) Date: Jun. 11, 2015

(87) PCT Pub. No.: WO2014/090301
PCT Pub. Date: Jun. 19, 2014

(65) Prior Publication Data
US 2016/0139086 A1 May 19, 2016

(51) Int. Cl.
*G01N 29/28* (2006.01)
*G01M 13/04* (2006.01)
*G01N 29/14* (2006.01)

(52) U.S. Cl.
CPC .......... *G01N 29/28* (2013.01); *G01M 13/04* (2013.01); *G01M 13/045* (2013.01);
(Continued)

(58) Field of Classification Search
CPC ........ G01N 29/28; G01N 29/14; G01N 29/04; G01N 29/2468; G01N 29/0655;
(Continued)

(56) References Cited

U.S. PATENT DOCUMENTS 2,427,348 A * 9/1947 Bond ............... B06B 1/067
310/326
3,296,195 A * 1/1967 Goossens ............. C07F 7/1896
525/477
(Continued)

FOREIGN PATENT DOCUMENTS

| EP | 1927855 A1 | 6/2008 |
| GB | 210955 A | 2/1924 |
| GB | 2109555 | * 6/1983 |

*Primary Examiner* — Helen Kwok
(74) *Attorney, Agent, or Firm* — Bryan Peckjian; SKF USA Inc. Patent Dept.

(57) ABSTRACT

A couplant and an arrangement of a couplant include a transducer and a construction component. The couplant is adapted to couple the transducer to a surface of the construction component. The couplant comprises basically 15% to 75% mass portion of hard metal.

19 Claims, 2 Drawing Sheets

(52) U.S. Cl.
CPC ....... *G01N 29/14* (2013.01); *G01N 2291/101* (2013.01); *G01N 2291/2696* (2013.01)

(58) Field of Classification Search
CPC .. G01N 29/2493; G01M 3/04; G01M 13/045; G01K 11/02; G01K 11/002
See application file for complete search history.

(56) References Cited

U.S. PATENT DOCUMENTS

| | | | | |
|---|---|---|---|---|
| 3,663,842 A * | 5/1972 | Miller | ............... | B06B 1/067 252/62 |
| 3,723,481 A * | 3/1973 | Bobear | ............... | C08K 3/0033 523/179 |
| 3,732,444 A * | 5/1973 | Miller | ............... | B06B 1/0655 310/336 |
| 3,763,694 A * | 10/1973 | Rathburn | ............... | G01N 29/28 73/644 |
| 3,826,127 A * | 7/1974 | Molina | ............... | G01N 29/28 252/960 |
| 3,921,442 A * | 11/1975 | Soloway | ............... | G01N 29/28 310/336 |
| 3,970,504 A * | 7/1976 | Palmer | ............... | C09J 183/04 156/329 |
| 4,069,083 A * | 1/1978 | Palmer | ............... | C09D 5/32 156/329 |
| 4,268,912 A * | 5/1981 | Congdon | ............... | H04R 17/00 310/337 |
| 4,293,477 A * | 10/1981 | Theodore | ............... | C08L 83/04 524/188 |
| 4,364,117 A * | 12/1982 | Snow | ............... | B06B 1/0607 367/152 |
| 4,435,985 A * | 3/1984 | Wickramasinghe | ... | G01N 29/06 73/606 |
| 4,556,813 A * | 12/1985 | Baumoel | ............... | G01F 1/662 310/334 |
| 4,559,827 A * | 12/1985 | Kupperman | ............... | G01N 29/28 73/644 |
| 4,665,750 A * | 5/1987 | Rogers | ............... | G10K 11/002 367/176 |
| 4,700,100 A * | 10/1987 | Congdon | ............... | B06B 1/0603 310/324 |
| 4,738,737 A * | 4/1988 | Runde | ............... | G01F 1/662 156/329 |
| 4,759,000 A * | 7/1988 | Reitz | ............... | G10K 11/205 181/286 |
| 4,929,368 A * | 5/1990 | Baumoel | ............... | C10M 107/38 156/333 |
| 5,038,615 A * | 8/1991 | Trulson | ............... | G01B 17/025 367/100 |
| 5,184,332 A * | 2/1993 | Butler | ............... | H04R 1/2842 181/160 |
| 5,515,733 A * | 5/1996 | Lynnworth | ............... | G01F 1/662 73/644 |
| 5,522,878 A * | 6/1996 | Montecalvo | ............... | A61N 1/04 600/437 |
| 5,770,801 A * | 6/1998 | Wang | ............... | A61B 8/0866 604/892.1 |
| 5,777,230 A * | 7/1998 | Vandervalk | ............... | B06B 1/0662 73/1.82 |
| 6,349,599 B1 * | 2/2002 | Lynnworth | ............... | G01N 29/223 73/644 |
| 6,941,819 B1 * | 9/2005 | Maki, Jr. | ............... | G01N 29/07 73/788 |
| 7,343,821 B2 * | 3/2008 | Panicke | ............... | G01F 1/662 73/644 |
| 9,435,770 B2 * | 9/2016 | Lamberton | ............... | G01N 29/2468 |
| 2005/0126293 A1 * | 6/2005 | Dasch | ............... | G01N 29/225 73/618 |
| 2009/0116775 A1 * | 5/2009 | Oguma | ............... | F16C 19/52 384/448 |
| 2009/0236937 A1 * | 9/2009 | Shiba | ............... | B06B 1/0603 310/322 |
| 2011/0214810 A1 * | 9/2011 | Burckhardt | ............... | C07C 251/08 156/331.1 |
| 2012/0053852 A1 * | 3/2012 | Padilla | ............... | G01N 29/07 702/34 |
| 2012/0157888 A1 * | 6/2012 | Grob | ............... | A61N 7/02 601/2 |
| 2012/0213036 A1 * | 8/2012 | Busch | ............... | B06B 1/0655 367/157 |
| 2013/0221805 A1 * | 8/2013 | Ogura | ............... | H01L 41/333 310/334 |
| 2015/0177197 A1 * | 6/2015 | Kojima | ............... | G10K 11/28 73/627 |
| 2015/0219527 A1 * | 8/2015 | Erskine | ............... | G01M 13/045 73/587 |
| 2017/0176398 A1 * | 6/2017 | Ziegler | ............... | G01N 29/28 |

\* cited by examiner

COUPLANT AND ARRANGEMENT OF COUPLANT, TRANSDUCER, AND CONSTRUCTION COMPONENT

CROSS REFERENCE TO RELATED APPLICATIONS

This is a United States National Stage Application claiming the benefit of International Application Number PCT/EP2012/075274 filed on 12 Dec. 2012, which is incorporated herein by reference in its entirety.

FIELD OF THE INVENTION

Embodiments of the present invention relate to monitoring of construction components in mechanical systems, more particularly but not exclusively to couplants of transducers or sensors in mechanical systems.

BACKGROUND

In mechanical systems monitoring of components can be very important. For example, roller bearings may suffer from abrasion and may cause severe damage to mechanical systems when they break down. Therefore, the deterioration of these components can be monitored using transducers or sensors. Such sensors may comprise piezoelectric components or semiconductors, which convert a mechanical or acoustic vibration or oscillation into an electrical signal. The electrical signal can then be processed, for example, a frequency analysis can be carried out, in order to detect frequencies which indicate an abrasion or deterioration of the respective components. For example, a roller bearing, as it wears out, may generate characteristic vibrations, which, once detected, may indicate a forthcoming breakdown of the bearing. Such a signal can then be used to generate a warning, especially when further components will be affected by the bearing breakdown.

The application of bearings and according monitoring systems as described above is very broad. For example, any kind of vehicles use a large number of bearings, such of which are used to bear critical components. For example, thinking of trains, their axes make use of bearings, which may cause severe accidents and damages, when they break down. Another application is, for example, power plants, such as off-shore wind power stations. The bearing of the rotors of such power stations is critical, especially when they are located off-shore, i.e. when they are not easily accessible. Therefore, there is a desire to monitor the bearing of such wind power stations in order to detect eventual failures early and to shut down the power station before severe damages occur. Steel works are another example of an application of the above transducer systems. Wherever bearings are used to bear components of power units, may they be rotors of wind power stations, axes of combustion engines or engines of conveyor belts, there is a desire to be informed of a forthcoming failure as soon as possible.

SUMMARY OF THE PRESENT INVENTION

Embodiments are based on the finding that acoustic emission transducers can be used for monitoring of construction components. It is a further finding that there is a desire to determine the sensitivity of a monitoring system in order to evaluate whether a given detection level should give cause for concern. Acoustic emission sensors can generally be designed to respond to motion normal to the surface on which they are applied, and can be manufactured as resonant devices to increase sensitivity around a frequency range of particular interest.

Embodiments are further based on the finding that the structural composition of such a device is critical for its sensitivity. In some embodiments a transducer may comprise a piezoelectric element with a certain geometry and mechanical resonances, which outputs an electrical signal. Such an electrical signal may then be pre-amplified and further processed. The further processing may include analog digital conversion, filtering, transformations, etc. Embodiments are further based on the finding that the sensitivity of a transducer is further influenced by the way such a transducer or sensor is coupled to the surface in question. In other words it is a finding that in any given situation poor coupling or bad choice of the couplant can lead to large drops in sensitivity. Hence, it is a further finding that the couplant of such a system is a major source of uncertainty in assessing the system sensitivity. This sensitivity may be fairly high level in laboratory conditions, however, when taking such measurements in the field, for example on vehicles or in power plants, it is not uncommon to see order of magnitude variations in the overall sensitivity.

It is a further finding that a couplant should remove air between the face of the transducer or sensor, and the respective surface of the construction component. It is a further finding that when air gets trapped due to the microstructure of the two contacting surfaces, the sensitivity of the transducer degrades. The acoustic impedance of air is far lower than that of the sensor face or test material and will cause considerable transmission losses at the interface. Moreover, it is a further finding that in addition to being of substantial higher acoustic impedance than air, a coupling layer should also be thin compared to the wavelength of the signal which is to be measured, as, for example, ultrasonic waves.

It is a further finding of embodiments that a hard metal introduced to the couplant can further lower the attenuation of the couplant between the transducer and the surface of the construction component. Acoustic emission may typically be measured in the frequency range of 100 to 500 kHz. The high frequency oscillations are hard to measure and therefore a good coupling between the sensor and the oscillation source may be desirable. If the coupling is not good, then the signal amplitude may decrease, which may in turn make it difficult to interpret these signals. The influencing factors are sensor geometry, couplant and surface properties of the target. Embodiments may provide a thread which allows mounting of sensors to a bearing housing, i.e. which allows generating a certain force or pressure between the surface of the sensor and the surface of the construction component.

Embodiments provide a couplant for coupling a transducer to a surface of a construction component. The couplant comprises basically 15 to 75% mass portion of hard metal. It is a finding that the portion of hard metal helps decreasing the impedance or the attenuation of the coupling layer between the transducer and the surface of a construction component, such as a housing of a bearing. Decreasing the attenuation allows for determining or detecting more reliable signals and hence may allow the system to be more reliable. Therewith, failures may be detected more reliably. The overall system may be made more robust. Furthermore, embodiments may allow detecting forthcoming failures of construction components sooner, such that further damages can be avoided more effectively.

Embodiments may provide the couplant with a mass portion of hard metal which is basically 30 to 35%, 32 to 34%, or 33%. In other words, it is a finding that a mass portion of hard metal of about ⅓ within the couplant, provides good coupling properties. That is to say when using about ⅓ of hard metal within the couplant, a low impedance or a low attenuation of the coupling layer can be realized. Hence, in some embodiments, basically one third of hard metal may be used within the couplant, where one third showed to be an advantageous combination.

In embodiments, the hard metal portion may comprise basically any hard metal. For example, the hard metal portion may comprise at least one of or a combination of the group of tungsten, W, tungsten carbide, W2C, WC, titanium nitride, TiN, titanium carbide, TiC, titanium carbide-nitride, Ti(C)N, titanium aluminum nitride, TiAlN, tantalum carbide TaC, cobalt, Co, and molybdenum, Mo. Embodiments can be based on the finding that such a hard metal may not be very compressive, therefore it elastically conducts the acoustic waves or vibrations through the couplant to the surface of the sensor or transducer. It is therefore a further finding that especially hard metals can provide low attenuation couplants. For example, a couplant using tungsten powder may provide the advantage that the attenuation as compared to the same couplant without tungsten powder can be decreased.

In embodiments the couplant may further comprise grease or a water-based gel. Such couplant can be used in embodiments that further have a mounting structure, such as a thread, a hole, a deepening, etc. for mounting the transducer or sensor and which may allow encapsulating the couplant. Such an encapsulation may as well be used to protect the couplant from other influences, such as salt water, e.g. when used in underwater application or in a vehicle exposed to de-icing salt, dust and dirt, heat, wetness, etc. Hence, in embodiments grease or gel can be used in the couplant together with the hard metal. For example, the transducer can be mounted using a thread or it can be screwed. In other embodiments, a clamp or a bracket can be used in order to mount the transducer to the construction component. Moreover, in some embodiments a spring can be used in order to provide a defined force between the transducer surface and the surface of the construction component.

In some embodiments the couplant can be used for hand measurement. In other words, a transducer is used to take occasional measurements on components, for example, for error control and trouble-shooting purposes. In such a scenario the couplant can be used in order to establish an acoustic coupling between the transducer and the component to be checked. In this scenario embodiments can enable a more reliable hand measurement. Moreover, as in conventional scenarios, high pressure or high force has to be applied to a transducer which is used for a hand measurement, this force can be reduced, as a better coupling can be achieved with the couplant at lower force.

In further embodiments, the couplant may as well comprise a curing material. In embodiments, the curing material may comprise at least one of or a combination of resin, epoxy, glue, PolyURrethane (PUR), silicone, adhesive, and sealing compound. In other words, it is a further finding of embodiments that a curing material such as a glue can be used in order to glue the transducer to the surface of the construction component. Moreover, the hard metal within the couplant is kept in place such that the low attenuation property of the couplant can be kept after curing the material, i.e. the curing material may avoid separation of the hard metal or changes in the concentration or distribution of the hard metal within the couplant. Embodiments may therewith provide the advantage that the transducer can be efficiently glued or mounted on the surface of a construction component while the hard metal within the couplant assures low attenuation or high coupling of acoustic waves between the surfaces of the construction component and the transducer. Embodiments may therefore provide the advantage that they make use of the synergy between the curing material and the hard metal within the same couplant.

In embodiments, the curing material when cured may have a hardness between basically 75 to 95 Shore D, 80 to 90 Shore D, or 84 to 86 Shore D. In other words, in embodiments, it may be advantageous to use a curing material with hardness within the above limits after curing, holding the hard metal powder or particles in place, such that an improved coupling of the two surfaces is achieved.

Embodiments further provide an arrangement of a transducer, a construction component and a couplant according to the above description. The transducer can be mounted to the construction component with the couplant between a surface of the construction component and a transducer. In some embodiments, the transducer can correspond to an acoustic emission sensor, which is coupled to the surface of the construction component. As described above, the couplant may then couple the two surfaces. In some embodiments, the transducer can be glued to the construction component with the couplant. In such embodiments, the synergy between the glue, offering an effective way to mount or attach the sensor to the target, and the hard metal within the couplant, allowing for a good acoustic coupling between the sensor and the surface, can be exploited.

In embodiments different transducer shapes may be utilized. For example, a transducer may have a flat transducer face or a rounded transducer face pointed towards a construction component. The rounded transducer face may correspond to a spherical or a partly spherical shape. In other words, embodiments may further exploit the finding that the surface shape of the transducer may affect the coupling. While a flat surface shape may provide a larger contact area, a rounded transducer face may enable a higher pressure in a small area. Embodiments may, in addition to the couplant and the hard metal, further make use of different transducer face shapes in order to further improve the coupling. In embodiments a transducer can be adapted to measure oscillations in a range of basically 1 kHz to 1 MHz, 10 kHz to 750 kHz or 100 kHz to 500 kHz. That is to say, that in embodiments a transducer may be adapted to measure acoustic waves as well as ultrasonic waves. Embodiments may therefore provide the advantage that a good coupling may be achieved with a coupling comprising the hard metal over a wide bandwidth. In embodiments, the construction component may correspond to a bearing, a roller bearing or a bearing housing. Moreover, in embodiments the construction component may be comprised in a vehicle, such as a train, a car, a bus, in a power plant, such as a wind power station, an underwater power station, a steelwork, an automotive application, in a conveyor system, in a steel mill, in a rolling mill, etc.

In some embodiments the construction component may be a casted construction component. In other words, the construction component may be a cast iron or other material part which has a rather low hardness compared to the hard metal within the couplant. Embodiments may therewith provide the advantage that even a vibration from a softer part, such as a cast part or piece, can be coupled to the sensor. By using the curing material in the couplant, the curing material can be adapted to the surface and to the material, such as cast iron, of the construction component. In other words, embodiments may provide the advantage that the curing material can be adapted to the construction component, such that the mechanical coupling of the transducer can be optimized. Moreover, the portion of the hard metal and the hard metal itself can be selected in a way such that an acoustic coupling is improved or even optimized at the same time.

In further embodiments the couplant is adapted to couple the transducer with a roller bearing such that oscillations of the roller bearing are detectable from an output signal of the transducer. In other words, some embodiments may comprise further electrical components, such as a preamplifier, an amplifier, a filter, a converter, any processing means, a processor, etc. in order to determine oscillations from the output signal of the transducer. Such oscillations may undergo further signal processing such as frequency analysis, filtering, analog-to-digital conversion, etc., in order to determine whether the roller bearing generates any suspicious vibrations or oscillations.

BRIEF DESCRIPTION OF THE FIGURES

Some other features or aspects will be described using the following non-limiting embodiments of apparatuses and/or methods by which of example only, and with reference to the accompanying Figures, in which.

DETAILED DESCRIPTION OF THE PRESENT INVENTION

Various embodiments will now be described in more detail with reference to the accompanying drawings. In the Figures, the thicknesses of lines, layers and/or regions may be exaggerated for clarity.

Accordingly, while embodiments are capable of various modifications and alternative forms, embodiments thereof are shown by way of example in the Figures and will herein be described in detail. It should be understood, however, that there is no intent to limit embodiments to the particular forms disclosed, but on the contrary, embodiments are to cover all modifications, equivalents, and alternatives falling within the scope of the invention.

Like numbers refer to like or similar elements throughout the description of the Figures. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

In the following description some components will be displayed in multiple Figures carrying the same reference signs, but may not be described multiple times in detail. A detailed description of a component may then apply to that component for all its occurrences.

Figure 1:
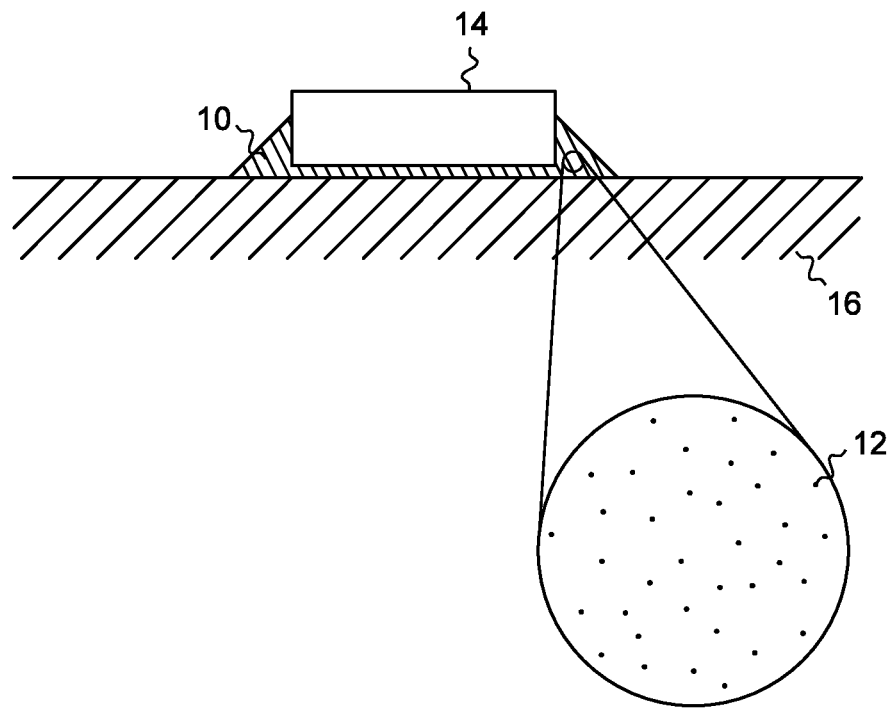
FIG. 1 illustrates an embodiment of an arrangement of a transducer, a couplant and a construction component.

FIG. 1 illustrates an embodiment of an arrangement of a transducer 14, a construction component 16 and a couplant 10. The transducer 14 is mounted to the construction component 16 with a couplant 10 between the surface of the construction component 16 and a transducer 14. The couplant 10 couples the transducer 14 to the surface of the construction component 16. The couplant 10 comprises basically 32 to 34% of tungsten in the present embodiment. The transducer 14 is implemented as an acoustic emission sensor and connected to the target 16 by the couplant 10. Moreover, it is assumed that the target surface, i.e. the surface of the construction component 16, has a roughness preferably between 0.8 µm Ra or a range of 0.2 to 1.6 µm Ra with a flat sensor 14 depending on the properties of the couplant. As FIG. 1 shows, in the present embodiment, it is assumed that the transducer 14 has a flat transducer face.

In the present embodiment, the couplant 10 comprises a curing material. The curing material comprises a resin. In other words, the connection between the sensor 14 and the target 16 is done by a resin system 10 with an approximate hardness of 85 Shore D, mixed with approximately ⅓ mass portion of tungsten powder. That is to say, the ratio between the resin and the tungsten powder corresponds to 2:1. The resin can correspond to epoxy resin. The epoxy resin couples the transducer 14 and the construction component 16. In other words, the couplant 10 is directly coupled to the surface of the transducer 14 and to the surface of the construction component 16.

In another embodiment, the sensor 14 can be screwed onto a construction component 16. In that case, instead of a curing material, a grease or water-based gel may be used comprising according hard metal portions. FIG. 1 depicts an embodiment wherein the transducer 14 is glued to the construction component 16 with the couplant 10. The magnification window 12 shows the hard metal particles or powder within the couplant. In the present embodiment, the acoustic emission sensor 14 is adapted to measure frequencies between 100 kHz and 500 kHz.

Figure 2:
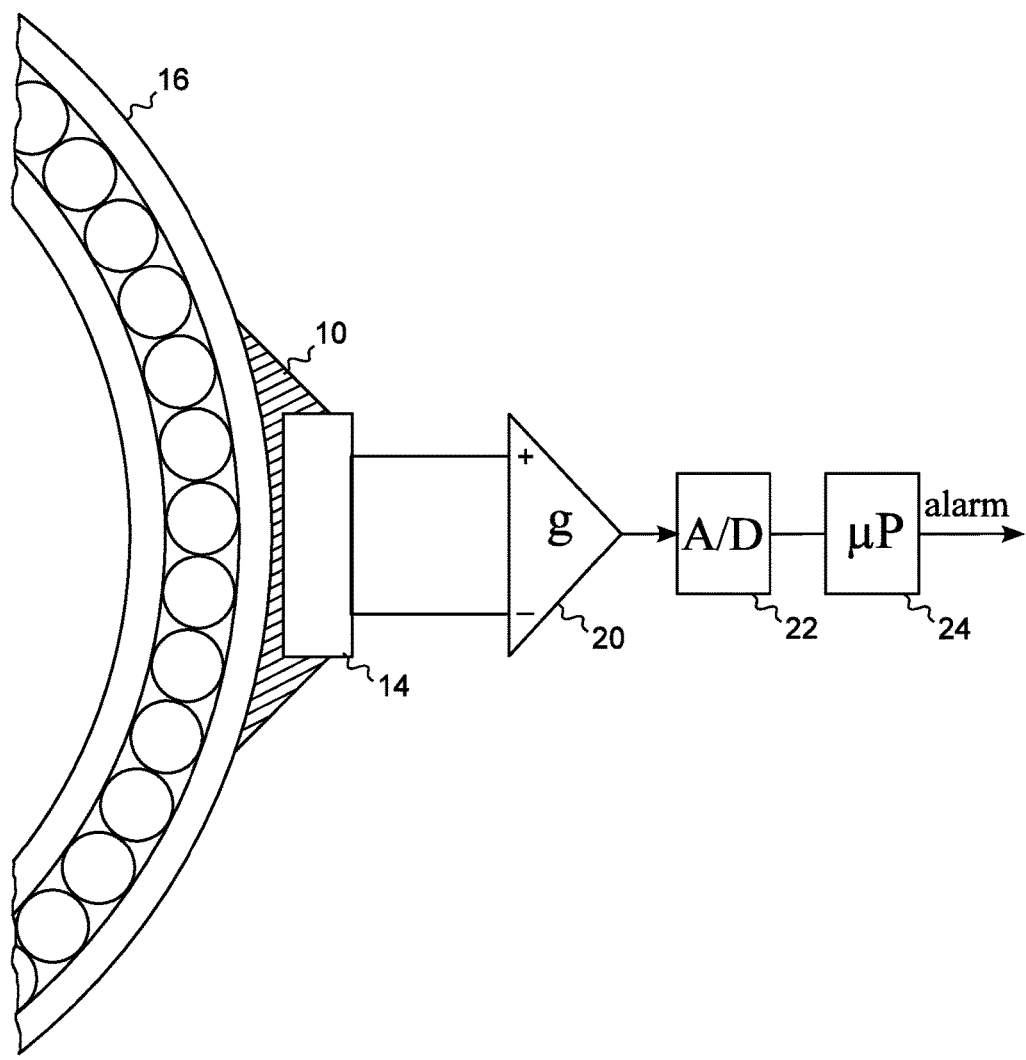
FIG. 2 illustrates another embodiment of an arrangement with accordingly adapted processing.

FIG. 2 illustrates another embodiment of an arrangement of a transducer 14, a construction component 16 and a couplant 10. As shown in FIG. 2, the construction component 16 corresponds to an outer ring 16 of a roller bearing to which the transducer 14, which is again implemented as an acoustic emission sensor 14, is glued using the couplant 10. In other embodiments, the transducer 14 can also be coupled using the couplant 10 to a bearing housing or any other housing. Such a housing may correspond to a casted construction component. In the embodiment shown in FIG. 2, the couplant 10 is adapted to couple the transducer 14 with the roller bearing 16 such that oscillations of the roller bearing are detectable from an output signal of the transducer 14. This is indicated in FIG. 2 by the further components 20, 22, 24. As illustrated by FIG. 2 the outputs of the acoustic emission sensor 14 are coupled to an amplifier 20 having an amplification gain of g. The output of the amplifier is then converted by the analog/digital converter 22 (A/D) before the digital samples are then further processed by the microprocessor 24 (μP). In the present embodiment, it is assumed that the frequency analysis is carried out by the microprocessor, looking for signal parts at frequencies, which are indicative of the roller bearing 16 to wear off, i.e. to a forthcoming breakdown. These frequency parts of the signals are then compared against a threshold, and if they exceed the threshold an according alarm signal is generated as indicated in FIG. 2.

Embodiments may provide the advantage that the coupling between the sensor 14 and the target 16 result in better signal amplitudes at the output of the sensor 14. Embodiments may therewith allow a use of less powerful and cheaper amplification electronics. Moreover, embodiments may allow for a more reliable detection of suspicious vibrations or oscillations in mechanical systems.

The description and drawings merely illustrate the principles of the invention. It will thus be appreciated that those skilled in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

REFERENCE SIGNS

10 Couplant
12 Hard metal
14 Transducer
16 Construction component
20 Amplifier
22 Analog/Digital converter
24 Micro processor

The invention claimed is:

1. A couplant for coupling a transducer to a surface of a construction component, the couplant comprising thirty percent (30%) to thirty-five percent (35%) mass portion of hard metal, the couplant further comprising a curing material containing an adhesive such that the couplant is configured to directly glue the transducer to the surface of the construction equipment, the couplant further comprising a grease such that the couplant can encapsulate the transducer onto the surface to protect the transducer from water such that the transducer can be used in an underwater application.

2. The couplant of claim 1, wherein the hard metal of the mass portion comprises cobalt (Co).

3. The couplant of claim 1, the hard metal of the mass portion comprises at least one of or a combination of the group of tungsten (W), tungsten carbide (W2C, WC), titanium nitride (TiN), titanium carbide (TiC), titanium carbide-nitride (Ti(C)N), titanium aluminum nitride (TiAlN), tantalum carbide (TaC), cobalt (Co), and molybdenum (Mo).

4. The couplant of claim 1, further comprising a water-based gel.

5. The couplant of claim 1, wherein the curing material comprises at least one of or a combination of resin, epoxy, glue, polyurethane (PUR), silicone, adhesive, and sealing compound.

6. The couplant of claim 1, wherein the curing material when cured has a hardness between 75 to 95 Shore D.

7. An arrangement of a transducer, a construction component and a couplant, comprising:
the couplant comprising thirty percent (30%) to thirty-five percent (35%) mass portion of hard metal, the couplant further comprising a curing material containing an adhesive such that the coupulant is configured to directly glue the transducer to the surface of the construction equipment, the transducer being glued to the construction component by the couplant with the couplant between a surface of the construction component and the transducer and the couplant placed over the transducer so as to encapsulate the transducer, the couplant further comprising a grease such that the couplant protects the transducer from water during use in an underwater application.

8. The arrangement of claim 7, further comprising a spring exerting a force on the transducer in the direction of the construction equipment.

9. The arrangement of claim 7, wherein wherein the hard metal of the mass portion comprises cobalt (Co).

10. The arrangement of claim 7, wherein the transducer has one of a flat transducer face or a rounded transducer face pointed towards the construction component.

11. The arrangement of claim 7, wherein the transducer is adapted to measure oscillations in a range of 1 kHZ to 1 MHz.

12. The arrangement of claim 7, wherein the construction component corresponds to one of a bearing, a roller bearing, or a bearing housing.

13. The arrangement of claim 7, wherein the construction component is a casted construction component.

14. The arrangement of claim 7, wherein the couplant is adapted to couple the transducer with a roller bearing such that oscillations of the roller bearing are detectable from an output signal of the transducer.

15. The couplant of claim 1, wherein the mass portion is 32%-34% mass portion of hard metal.

16. The couplant of claim 1, wherein the curing material when cured has a hardness between 80 to 90 Shore D.

17. The couplant of claim 1, wherein the curing material when cured has a hardness between 84 to 86 Shore D.

18. The arrangement of claim 7, wherein the transducer is adapted to measure oscillations in a range of 10 kHz to 750 kHz.

19. The arrangement of claim 7, wherein the transducer is adapted to measure oscillations in a range of 100 kHz to 500 kHz.

* * * * *